US00PP22018P2

(12) United States Plant Patent
Heuger

(10) Patent No.: US PP22,018 P2
(45) Date of Patent: Jul. 5, 2011

(54) ***HELLEBORUS* PLANT NAMED 'COSEH 750'**

(50) Latin Name: *Helleborus×nigercors*
Varietal Denomination: COSEH 750

(76) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 12/798,348

(22) Filed: Mar. 31, 2010

(51) Int. Cl.
*A01H 5/00* (2006.01)

(52) U.S. Cl. ..... Plt./439
(58) Field of Classification Search ..... Plt./439
See application file for complete search history.

*Primary Examiner* — Annette H Para
(74) *Attorney, Agent, or Firm* — C. A. Whealy

(57) ABSTRACT

A new and distinct cultivar of *Helleborus* plant named 'COSEH 750', characterized by its upright and outwardly arching plant habit; uniform flowering habit; dark green-colored leaves; long flowering period; numerous single light green to white-colored flowers; and good garden performance.

2 Drawing Sheets

Botanical designation: *Helleborus×nigercors*.
Cultivar denomination: 'COSEH 750'.

BACKGROUND OF THE INVENTION

The present invention relates to a new and distinct cultivar of *Helleborus* plant, botanically known as *Helleborus×nigercors*, and hereinafter referred to by the name 'COSEH 750'.

The new *Helleborus* plant is a product of a planned breeding program in Glandorf, Germany. The objective of the breeding program was to create new uniform *Helleborus* cultivars with unique and attractive flower coloration and resistance to pests.

The new *Helleborus* plant originated from a cross-pollination conducted by the Inventor in Glandorf, Germany in November, 2002 of two unnamed proprietary seedling selections of *Helleborus×nigercors*, not patented. The new *Helleborus* plant was discovered and selected by the Inventor as a single flowering plant from within the progeny of the stated cross-pollination grown in a controlled greenhouse environment in Glandorf, Germany in February, 2005.

Asexual reproduction of the new *Helleborus* plant by divisions in a controlled greenhouse environment in Glandorf, Germany since March, 2005, has shown that the unique features of this new *Helleborus* plant are stable and reproduced true to type in successive generations.

SUMMARY OF THE INVENTION

Plants of the new *Helleborus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'COSEH 750'. These characteristics in combination distinguish 'COSEH 750' as a new and distinct cultivar of *Helleborus* plant:

1. Upright and outwardly arching plant habit.
2. Uniform flowering habit.
3. Dark green-colored leaves.
4. Long flowering period.

5. Numerous single light green to white-colored flowers.
6. Good garden performance.

Compared to plants of the parent selections, plants of the new *Helleborus* flower more freely and more uniformly.

Plants of the new *Helleborus* can be compared to plants of *Helleborus niger×Helleborus lividus* 'COSEH 700', disclosed in U.S. Plant Pat. No. 21,003. Plants of the new *Helleborus* differ primarily from plants of 'COSEH 700' in the following characteristics:

1. Plants of the new *Helleborus* have lighter green-colored leaves than plants of 'COSEH 700'.
2. Plants of the new *Helleborus* and 'COSEH 700' differ in flower color.

BRIEF DESCRIPTION OF THE PHOTOGRAPHS

The accompanying colored photographs illustrate the overall appearance of the new *Helleborus* plant, showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'COSEH 750' grown in a container.

The photograph on the second sheet is a close-up view of a typical flower of 'COSEH 750'.

DETAILED BOTANICAL DESCRIPTION

The aforementioned photographs and following observations, measurements and values describe plants grown in Glandorf, Germany in 1.5-liter containers during the winter in a glass-covered greenhouse and under conditions which closely approximate commercial *Helleborus* production. During the production of the plants, day temperatures ranged from 12° C. to 32° C. and night temperatures ranged from 3° C. to 18° C. Plants were one year old when the photographs and the description were taken. In the following description, color references are made to The Royal Horticultural Society Colour Chart, 2007 Edition, except where general terms of ordinary dictionary significance are used.

Botanical classification: *Helleborus×nigercors* 'COSEH 750'.

Parentage:

*Female, or seed, parent.*—Unnamed proprietary seedling selection of *Helleborus×nigercors*, not patented.

*Male, or pollen, parent.*—Unnamed proprietary seedling selection of *Helleborus×nigercors*, not patented.

Propagation:

*Type.*—By tissue culture.

*Time to initiate roots.*—About two months at 12° C.

*Time to produce a rooted young plant.*—About six months at 4° C. to 15° C.

*Root description.*—Thick to thin, fleshy; white to brown in color.

*Rooting habit.*—Sparse.

Plant description:

*Plant form and growth habit.*—Herbaceous perennial; upright and outwardly arching plant habit with flowers held above the foliar plane; shape, globular; moderately vigorous growth habit.

*Plant height.*—About 25.2 cm.

*Plant diameter* (*area of spread*).—About 39.9 cm.

Foliage description:

*Arrangement.*—Leaves arranged in a basal rosette; palmately compound with five leaflets per leaf.

*Leaf length.*—About 19.2 cm.

*Leaf width.*—About 22.6 cm.

*Leaflet length.*—About 12.6 cm.

*Leaflet width.*—About 5 cm.

*Leaf shape.*—Palmate; orbicular in outline.

*Leaflet shape.*—Elliptic to ovate; lower leaves occasionally cleft.

*Leaflet apex.*—Acute.

*Leaflet base.*—Attenuate.

*Leaflet margin.*—Sharply serrate.

*Leaflet texture, upper and lower surfaces.*—Smooth, glabrous; leathery.

*Leaflet venation pattern.*—Pinnate.

*Leaflet color.*—Developing leaves, upper surface: Close to 137A to 137B; base tinged with close to 183B to 183C. Developing leaves, lower surface: Close to 147B to 147C. Fully developed leaves, upper surface: Close to 147A; venation, close to 143A to 143B. Fully developed leaves, lower surface: Close to 147B; venation, close to 144C.

*Petiole.*—Length: About 8.4 cm. Diameter: About 7 mm. Texture, upper and lower surfaces: Smooth, glabrous. Color, upper and lower surfaces: Close to 144A; base tinged with close to 177A.

Flower description:

*Flower shape and habit.*—Single rotate flowers; uniform flowering habit; about seven flowers per terminal cyme; flowers facing slightly outwardly to nodding.

*Fragrance.*—None detected.

*Natural flowering season.*—Long flowering period; plants flower from winter to early spring in Germany.

*Flower longevity on the plant.*—About ten days; flowers not persistent.

*Flower buds.*—Length: About 1.9 cm. Diameter: About 1.3 cm. Shape: Ovate. Color: Close to 145C.

*Inflorescence height.*—About 39.9 cm.

*Inflorescence diameter.*—About 22.4 cm.

*Flower diameter.*—About 7.3 cm.

*Flower depth* (*height*).—About 2.6 cm.

*Petals.*—Transformed into nectaries.

*Sepals.*—Arrangement: About five in a single whorl. Length: About 3.6 cm. Width: About 2.8 cm. Shape: Broadly elliptic to broadly obovate. Apex: Rounded to emarginate. Margin: Entire. Texture, upper and lower surfaces: Smooth, glabrous. Color: When opening, upper and lower surfaces: Close to 145C; towards the base, close to 144C. Fully opened, upper and lower surfaces: Close to 157A towards the base, close to 144C to 144D.

*Peduncles.*—Strength: Moderately strong. Length: About 32.5 cm. Diameter: About 1.1 cm. Aspect: About 10° from vertical. Texture: Smooth, glabrous. Color: Close to 145A.

*Pedicels.*—Strength: Moderately strong. Length: About 3.4 cm. Diameter: About 2.5 mm. Aspect: About 30° from the peduncle axis. Texture: Smooth, glabrous. Color: Close to 145B to 145C.

*Reproductive organs.*—Stamens: Quantity per flower: About 70. Filament length: About 1.1 cm. Filament color: Close to 155C. Anther shape: Narrowly reniform. Anther length: About 1.5 mm. Anther color: Close to 157B. Pollen amount: Scarce. Pollen color: Close to 158D. Pistils: Quantity per flower: About five. Pistil length: About 1.2 cm. Stigma shape: Club-shaped. Stigma color: Close to N144D. Style length: About 1.1 cm. Style color: Close to 145C. Ovary color: Close to 145A to 145B. Nectaries (transformed petals): Quantity per flower: About 15. Length: About 9 mm. Diameter, apex: Close to 2 mm. Diameter, base: Close to 1 mm. Shape: Flattened triangular. Color: Close to 151A to 151B; towards the base, close to 144B.

*Seeds/fruits.*—Seed and fruit development have not been observed.

Garden performance: Plants of the new *Helleborus* have been observed to have good garden performance and to tolerate rain, wind and temperatures ranging from about −10° C. to about 35° C.

Pathogen/pest resistance: Plants of the new *Helleborus* have not been shown to be resistant to pathogens and pests common to *Helleborus*.

It is claimed:

1. A new and distinct *Helleborus* plant named 'COSEH 750' as illustrated and described.

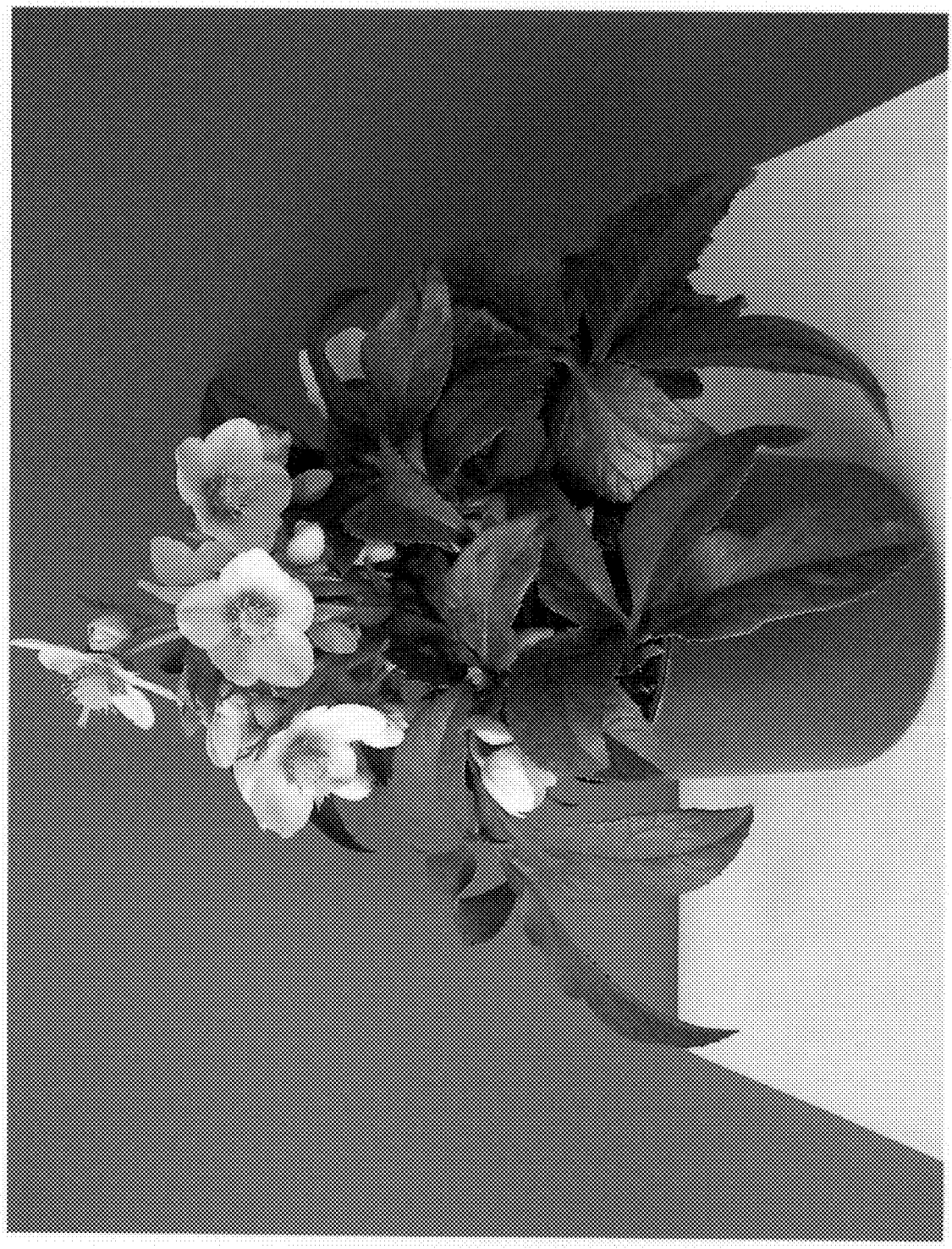

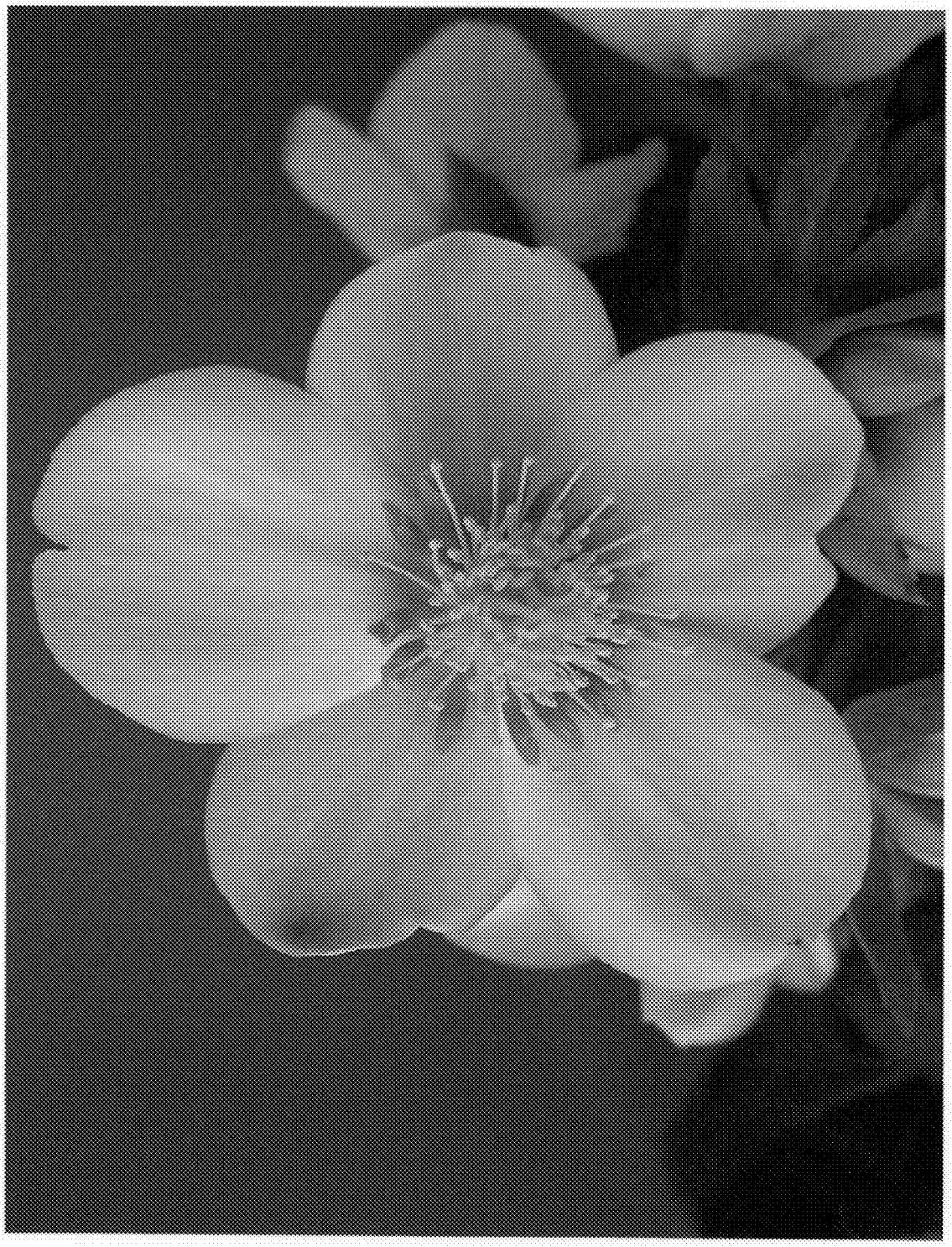

* * * * *